US008945196B2

(12) United States Patent
Huttemann et al.

(10) Patent No.: US 8,945,196 B2
(45) Date of Patent: Feb. 3, 2015

(54) LIGHT THERAPY TREATMENT

(75) Inventors: Maik Huttemann, Grosse Pointe Park, MI (US); Icksoo Lee, Grosse Pointe Park, MI (US); John Kamholz, Grosse Pointe Woods, MI (US); Lawrence Grossman, Ann Arbor, MI (US); Karin Przyklenk, Grosse Pointe Park, MI (US); Thomas Sanderson, Ypsilanti, MI (US)

(73) Assignee: Wayne State University, Detroit, MI (US)

( * ) Notice: Subject to any disclaimer, the term of this patent is extended or adjusted under 35 U.S.C. 154(b) by 525 days.

(21) Appl. No.: 12/771,137

(22) Filed: Apr. 30, 2010

(65) Prior Publication Data

US 2011/0066213 A1    Mar. 17, 2011

Related U.S. Application Data

(60) Provisional application No. 61/215,105, filed on May 1, 2009.

(51) Int. Cl.
  *A61N 5/06* (2006.01)
(52) U.S. Cl.
  CPC ....... *A61N 5/0613* (2013.01); *A61N 2005/0643* (2013.01); *A61N 2005/0652* (2013.01); *A61N 2005/0659* (2013.01)
  USPC .......................... 607/88; 607/89; 606/2; 606/3
(58) Field of Classification Search
  USPC ....................................... 606/2, 3; 607/88, 89
  See application file for complete search history.

(56) References Cited

U.S. PATENT DOCUMENTS

| 4,930,504 | A | * | 6/1990 | Diamantopoulos et al. .... 607/88 |
| 4,966,144 | A | | 10/1990 | Rochkind et al. |
| 5,259,380 | A | | 11/1993 | Mendes et al. |
| 5,464,436 | A | | 11/1995 | Smith |
| 5,616,140 | A | | 4/1997 | Prescott |
| 5,989,245 | A | | 11/1999 | Prescott |
| 6,214,035 | B1 | * | 4/2001 | Streeter .......................... 607/89 |
| 6,267,780 | B1 | | 7/2001 | Streeter |
| 6,273,905 | B1 | | 8/2001 | Streeter |

(Continued)

FOREIGN PATENT DOCUMENTS

| EP | 0130950 A2 | 1/1985 |
| WO | WO-2009117323 A2 | 9/2009 |

OTHER PUBLICATIONS

International Search Report for PCT/US2010/033175 dated Jul. 23, 2010.

*Primary Examiner* — Tod T Van Roy
(74) *Attorney, Agent, or Firm* — Rader, Fishman & Grauer PLLC

(57) ABSTRACT

An exemplary method includes selecting at least one light source configured to generate light at a particular wavelength and applying the light to tissue following an ischemic event. Applying the light to the tissue inhibits cytochrome c oxidase activity. Another exemplary method includes selecting at least one light source configured to generate light at a particular wavelength and applying the light to tissue following an ischemic event and prior to either reoxygenation of the tissue or clinical intervention to reduce cell damage. An exemplary light therapy device includes at least one light source configured to generate light having a wavelength of at least one of approximately 730-770 nm, 850-890 nm, 880-920 nm, and 930-970 nm.

18 Claims, 6 Drawing Sheets

(56) References Cited

U.S. PATENT DOCUMENTS

| | | |
|---|---|---|
| 6,290,714 B1 | 9/2001 | Streeter |
| 6,312,451 B1 | 11/2001 | Streeter |
| 6,395,016 B1 | 5/2002 | Oron et al. |
| 6,443,974 B1 | 9/2002 | Oron et al. |
| 6,537,304 B1 | 3/2003 | Oron |
| 6,690,958 B1 | 2/2004 | Walker et al. |
| 6,918,922 B2 | 7/2005 | Oron |
| 7,051,738 B2 | 5/2006 | Oron et al. |
| 7,107,997 B1 | 9/2006 | Moses et al. |
| 7,303,578 B2 | 12/2007 | De Taboada et al. |
| 7,309,348 B2 | 12/2007 | Streeter et al. |
| 7,316,922 B2 | 1/2008 | Streeter |
| 7,344,555 B2 | 3/2008 | Anders et al. |
| 7,351,253 B2 | 4/2008 | DiMauro et al. |
| 7,354,432 B2 | 4/2008 | Eells et al. |
| 7,534,255 B1 | 5/2009 | Streeter et al. |
| 7,575,589 B2 | 8/2009 | De Taboada et al. |
| 2002/0068927 A1 | 6/2002 | Prescott |
| 2002/0183809 A1 | 12/2002 | Oron et al. |
| 2003/0004499 A1 | 1/2003 | McDaniel |
| 2003/0109906 A1 | 6/2003 | Streeter |
| 2003/0181962 A1 | 9/2003 | Streeter |
| 2003/0212442 A1 | 11/2003 | Streeter |
| 2003/0216797 A1 | 11/2003 | Oron |
| 2004/0039269 A1 | 2/2004 | Ward et al. |
| 2004/0153130 A1 | 8/2004 | Oron et al. |
| 2004/0210275 A1 | 10/2004 | Town et al. |
| 2004/0220513 A1 | 11/2004 | Streeter |
| 2004/0260367 A1 | 12/2004 | De Taboada et al. |
| 2005/0019744 A1 | 1/2005 | Bertuglia |
| 2005/0020595 A1 | 1/2005 | Kalish et al. |
| 2005/0107851 A1 | 5/2005 | Taboada et al. |
| 2005/0171414 A1 | 8/2005 | Demos et al. |
| 2005/0197681 A1* | 9/2005 | Barolet et al. ............... 607/86 |
| 2006/0064504 A1 | 3/2006 | Rechterman et al. |
| 2006/0217787 A1 | 9/2006 | Olson et al. |
| 2006/0241726 A1 | 10/2006 | Whitehurst |
| 2006/0253177 A1 | 11/2006 | Taboada et al. |
| 2007/0038269 A1 | 2/2007 | Whitehurst |
| 2007/0073366 A1 | 3/2007 | Porco |
| 2007/0179570 A1 | 8/2007 | De Taboada et al. |
| 2007/0179571 A1 | 8/2007 | De Taboada et al. |
| 2008/0009689 A1 | 1/2008 | Benaron et al. |
| 2008/0033412 A1 | 2/2008 | Whelan et al. |
| 2008/0058881 A1 | 3/2008 | Wagner et al. |
| 2008/0131968 A1 | 6/2008 | Bornstein |
| 2008/0139908 A1 | 6/2008 | Kurth |
| 2008/0139992 A1 | 6/2008 | Bornstein |
| 2009/0216301 A1 | 8/2009 | Streeter et al. |
| 2009/0254154 A1 | 10/2009 | De Taboada et al. |
| 2009/0299441 A1* | 12/2009 | Bornstein ............... 607/89 |
| 2010/0087719 A1 | 4/2010 | Benni |

* cited by examiner

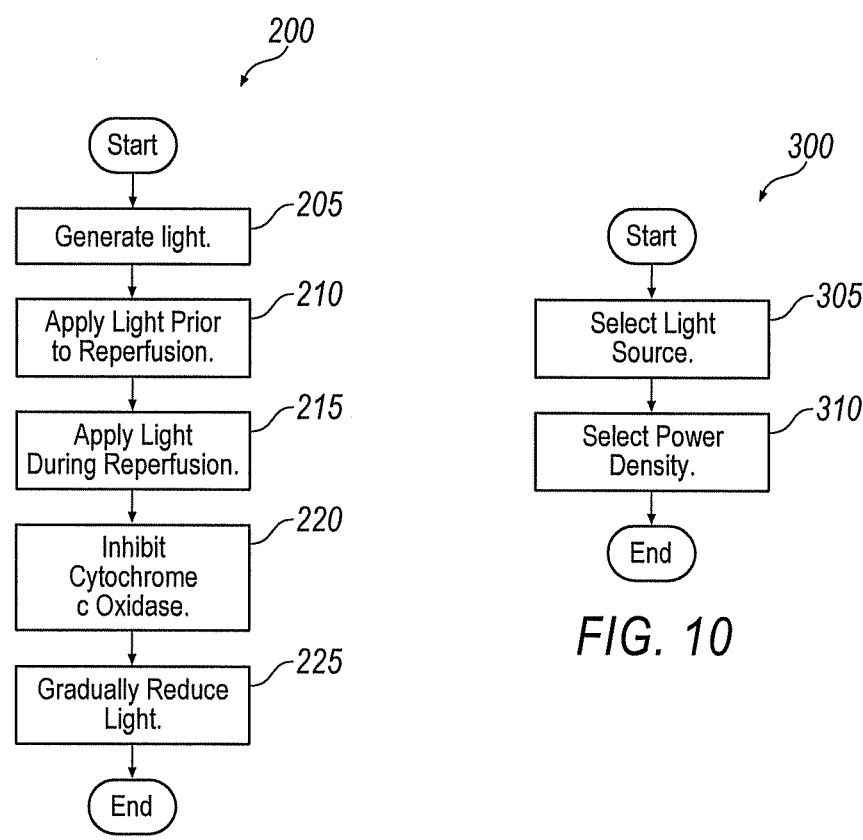

US 8,945,196 B2

LIGHT THERAPY TREATMENT

CROSS-REFERENCE TO RELATED APPLICATIONS

This application claims the benefit of U.S. application Ser. No. 61/215,105 filed on May 1, 2009, the contents of which are incorporated herein in their entirety.

BACKGROUND

An ischemic event occurs when the supply of oxygen and nutrients to an organ or tissue is restricted. For example, the interruption of blood flow to regions of the brain and heart results in myocardial and cerebral ischemia, respectively. Timely restoration of oxygen and nutrients, termed reperfusion, is essential for the survival of the ischemic organ or tissue. However, despite the benefits of this reintroduction of oxygen to ischemic tissue, reperfusion per se can also precipitate tissue death. The mechanisms of this phenomenon, termed reperfusion injury, are complex but involve the formation of cytotoxic oxygen-derived free radicals also called reactive oxygen species that can exacerbate death and dysfunction of previously ischemic tissue. Accordingly, an apparatus and method that limit the production of reactive oxygen species during reperfusion, and thus attenuating lethal reperfusion injury and maximizing the benefits of timely reperfusion is needed.

BRIEF DESCRIPTION OF THE DRAWINGS

FIG. 9 illustrates an exemplary flowchart of a process that may be used to reduce the risk of reperfusion injury following an ischemic event.

FIG. 10 illustrates an exemplary flowchart of a process that may be used to design a device configured to inhibit cytochrome c oxidase, such as the exemplary light therapy device illustrated in FIG. 8.

DETAILED DESCRIPTION

Figure 1:
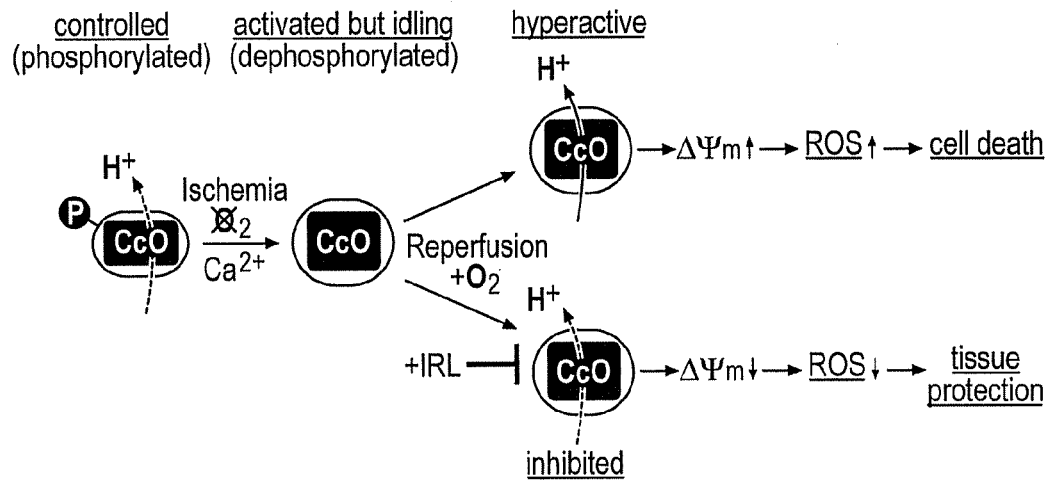
FIG. 1 illustrates an exemplary model of tissue protection through inhibition of cytochrome c oxidase with infrared light during reperfusion.

The treatment described herein may be used to limit the production of reactive oxygen species or reactive oxygen and nitrogen species generated during, for example, reoxygenation or reperfusion of ischemic tissue. As described herein, ischemia is defined as the restriction of oxygen and nutrients to an organ or tissue. Reperfusion is defined as the process where oxygen and other nutrients are restored to ischemic tissue. The onset of reperfusion is defined as the instant in which reperfusion begins either naturally or as a result of clinical intervention. The inventors have discovered that applying the disclosed treatment at before, during, and/or after reoxygenation (e.g., prior to and during the initial minutes-hours of reperfusion) may reduce cell death and cell damage caused by, for instance, reperfusion injury following an ischemic event. Accordingly, an exemplary process includes applying light to an ischemic area of tissue before reperfusion and during the initial minutes-hours of reperfusion. The onset of reperfusion may be initiated by clinical intervention such as administering a clot-busting drug, inflating/deflating an angioplasty balloon, resuscitation, transfusion, or administering vaso-active drugs, among others. Therefore, in another exemplary approach, an exemplary process includes applying light to an ischemic area of tissue before, during, and/or after the initiation of clinical intervention following an ischemic event. In any event, the inventors believe that applying light with the appropriate wavelength or wavelengths to the ischemic area at the appropriate time or times directly or indirectly inhibits cytochrome c oxidase. As discussed in greater detail below, it is believed that this direct or indirect inhibition of cytochrome c oxidase indirectly reduces the production of reactive oxygen species, resulting in reduced cell damage and cell death caused by reperfusion injury. It is possible that another mechanism besides inhibiting cytochrome c oxidase causes the reduction in reactive oxygen species production. Moreover, multiple mechanisms, of which reducing cytochrome c oxidase activity may be one, could be responsible for reduced reactive oxygen species production. For instance, the treatment described herein may inhibit the terminal step of the electron transport chain (i.e., the electron transfer from cytochrome c to cytochrome c oxidase to molecular oxygen). Further, the treatment described herein may result in other benefits in addition to or besides the reduction of reactive oxygen species.

Organs in the body depend on aerobic energy provided by the mitochondrial oxidative phosphorylation process (OxPhos). In instances of myocardial ischemia, cerebral ischemia, and other instances where blood supply and/or oxygen is reduced in tissue, energy is depleted in the affected areas. Cellular response to this stressed situation includes the release of calcium, leading to activation of mitochondrial proteins, likely mediated through protein dephosphorylation. However, during ischemia, OxPhos cannot proceed due to the lack of its terminal substrate, oxygen. Upon reperfusion, oxygen and other nutrients reach the stressed mitochondria. However, it is believed that a substantial fraction of cellular damage occurs at the onset of reperfusion due to hyperactive OxPhos enzymes. Namely, while attempting to restore energy levels, OxPhos complexes generate pathologically high mitochondrial membrane potentials (i.e., a transient hyperpolarization of the mitochondrial membrane potential), a condition known to lead to the excessive production of reactive oxygen species. Reactive oxygen species trigger cellular death processes during reperfusion, thus producing extensive damage to the affected tissues. Accordingly, the treatment described herein may be used to modulate mitochondrial function in vivo and limit the production of reactive oxygen species during reperfusion of tissue, such as the heart or brain.

In one exemplary approach, mitochondrial function may be modulated by down-regulation of OxPhos through non-pharmacological inhibition of the OxPhos step catalyzed by cytochrome c oxidase, i.e., the electron transfer from cytochrome c to cytochrome c oxidase to oxygen, using infrared light. This non-invasive modulation of OxPhos using infrared light may protect tissues, such as the heart or brain, from ischemia and/or reperfusion injury. Moreover, the direct or indirect inhibition of cytochrome c oxidase may reduce the mitochondrial membrane potential during reperfusion and subsequently attenuate reperfusion-induced reactive oxygen species generation, which is a likely underlying mechanism for infrared light mediated cardio- and neuro-protection.

Studies have shown that cardiovascular and cerebrovascular disease, including cardiac ischemia as a consequence of acute myocardial infarction and brain ischemia resulting from cardiac arrest or stroke, remain leading causes of death and disability. Established treatments to limit tissue damage caused by myocardial and cerebral ischemia include promptly restoring oxygen delivery to the ischemic areas. However, while timely reflow helps salvage ischemic cells including cardiomyocytes and neurons, reperfusion can also precipitate significant, irreversible tissue damage, and thus offset some of the benefits of reperfusion. Moreover, reperfusion can contribute to death and disability following acute myocardial infarction, stroke, and resuscitation/return of spontaneous circulation.

Previous attempts to attenuate myocardial ischemia-reperfusion injury in the heart and brain have focused on pharmacological therapies to scavenge reactive oxygen species. These pharmacological therapies have yielded inconsistent results in experimental models and have failed to translate into clinical therapies. As far as the inventors are aware, previous attempts to use light therapy following an ischemic event failed because the light in the previous treatments was applied at the wrong time and had a wavelength that increased cytochrome c oxidase activity, which may have caused further cell damage and death.

To the contrary, the exemplary treatment described herein reduces the production of reactive oxygen species rather than only scavenging reactive oxygen species. Specifically, when the appropriate wavelengths of light are selected and when the light is applied at the appropriate time relative to reoxygenation, infrared light treatment has been shown to reduce infarct size following acute myocardial infarction and reduce the extent of neurological deficits following brain ischemia.

A main photoacceptor of infrared light is mitochondrial cytochrome c oxidase. Dimeric cytochrome c oxidase is a 26-subunit enzyme that can adjust energy production to demand and is regulated by phosphorylation and the cellular ATP/ADP ratio. Cytochrome c oxidase is the terminal enzyme and proposed rate-limiting complex of the mammalian electron transport chain under physiological conditions. Cytochrome c oxidase contains several chromophores, including two copper and two heme centers, that are involved in enzyme catalysis and have been suggested to function as the primary photoacceptors for infrared light. In addition, amino acids involved in proton pumping may also be photomodulated. Cytochrome c, which delivers electrons to cytochrome c oxidase and contains a heme group may also be a photoacceptor of infrared light that may contribute to the overall effect on cytochrome c oxidase activity.

The inventors hypothesize that cytochrome c oxidase responds differently to different wavelengths of infrared light. Indeed, the inventors have identified wavelengths of light that are believed to directly or indirectly inhibit cytochrome c oxidase, which in turn indirectly reduces production of reactive oxygen species. One way to identify wavelengths of light that inhibit cytochrome c oxidase is to scan the near infrared wavelengths and, in parallel, analyze the effect on cytochrome c oxidase activity. A treatment that incorporates the wavelengths identified to inhibit cytochrome c oxidase may also inhibit respiration in a reversible and switch-like manner.

The inventors believe that one mechanism regulating the activity of the electron transport chain complexes may be via the mitochondrial membrane potential. When the mitochondrial membrane potential is high, further proton pumping is inhibited. A decrease in the mitochondrial membrane potential through proton utilization by ATP synthase may allow the electron transport chain to pump protons. As an extension to that classical model, the cell signaling pathways also control the activity of the electron transport chain complexes. This in turn controls the mitochondrial membrane potential, maintaining healthy, low mitochondrial membrane potential levels between, for instance, 80-140 mV. Such regulation helps higher organisms because the mitochondrial membrane potential is directly related to the production of reactive oxygen species. When the mitochondrial membrane potential is greater than, for instance, 140 mV, reactive oxygen species production increases exponentially. Mitochondria of resting cells with healthy or lower mitochondrial membrane potential levels do not produce significant amounts of reactive oxygen species. Thus, the maintenance of physiologically low mitochondrial membrane potential values avoids excess generation of reactive oxygen species but provides the capability to produce ATP because maximal rates of ATP synthesis by ATP synthase occur when mitochondrial membrane potential levels are, for instance, between 100 and 120 mV.

Stress conditions such as ischemia lead to the release of calcium, disruption of mitochondrial function, and differential phosphorylation, especially dephosphorylation of many mitochondrial proteins, which may be mediated by calcium-activated phosphatases, which can lead to cell death. Referring to FIG. 1, during ischemia, excessive calcium may be released leading to an activated state of OxPhos complexes including cytochrome c oxidase. However, since oxygen, the substrate of cytochrome c oxidase, is absent, the OxPhos process cannot proceed. During reperfusion in the presence of oxygen, maximal electron transfer rates occur due to hyper-activated OxPhos, followed by sharply increased mitochondrial membrane potential levels at which excessive reactive oxygen species production occurs. High reactive oxygen species levels may overwhelm endogenous antioxidant enzymes and cause irreparable damage to the cell. Thus, reactive oxygen species play a role in ischemia-reperfusion injury.

In normoxia, cytochrome c oxidase activity is down-regulated via phosphorylation. During ischemia, cytochrome c oxidase becomes differentially phosphorylated or dephosphorylated but cannot operate due to the lack of oxygen. At the onset of reperfusion and in the presence of oxygen, the electron transport chain proton pumps operate at maximal activity, creating high mitochondrial membrane potentials, leading to the production of excessive reactive oxygen species. Transient inhibition of cytochrome c oxidase with infrared light avoids increased mitochondrial membrane potential levels and the production of reactive oxygen species, and thus avoids cell death during reperfusion.

Figure 2A:
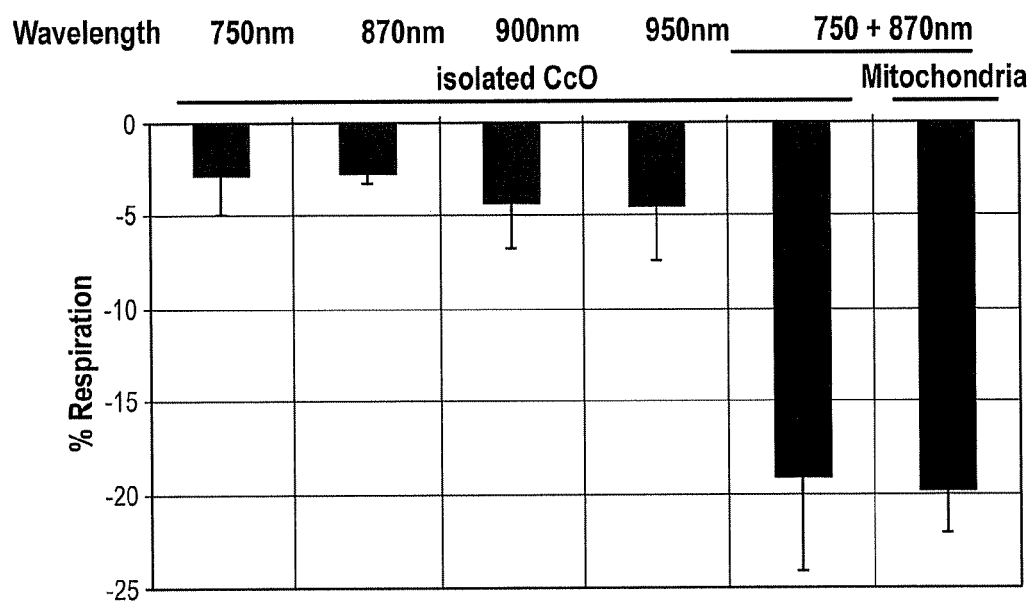
FIG. 2A illustrates an exemplary graph showing the effects of four exemplary wavelengths of infrared light emitted by low power diodes on isolated cytochrome c oxidase and mitochondria.
Figure 2B:
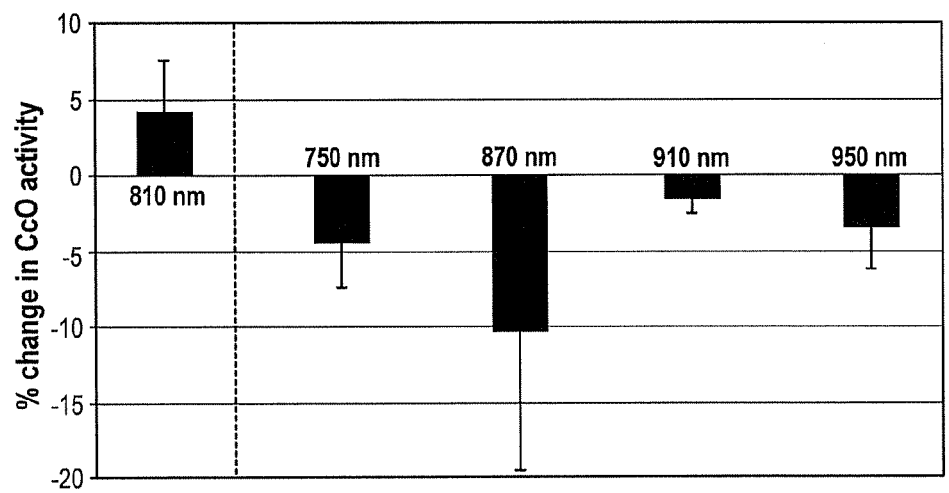
FIG. 2B illustrates an exemplary graph showing the effects of five exemplary wavelengths of infrared light emitted by high power diodes on isolated cytochrome c oxidase.

FIGS. 2A and 2B are graphs illustrating the effects of various wavelengths of infrared light emitted by low power diodes (FIG. 2A) and high power diodes (FIG. 2B) on cytochrome c oxidase activity based on experiments performed by the inventors. The inventors have discovered that light with a wavelength within the ranges of approximately 730-770 nm, 850-890 nm, 880-920 nm, or 930-970 nm directly or indirectly inhibits cytochrome c oxidase. In support of this discovery, FIG. 2A illustrates the effects that wavelengths of approximately 750 nm, 870 nm, 900 nm, and 950 nm have on cytochrome c oxidase activity. However, any frequency within the ranges previously mentioned is believed to have a similar effect on cytochrome c oxidase activity. Thus, any wavelength specifically mentioned herein is intended to include a range of wavelengths at least +/−20 nm from the specific wavelength disclosed. For instance, FIG. 2B illustrates that a wavelength of 910 nm has a similar effect on cytochrome c oxidase activity as a wavelength of 900 nm.

Additional frequencies that inhibit cytochrome c oxidase may be identified by integrating a customized light-protected oxygen electrode chamber with infrared light-permeable quartz windows into a double beam spectrophotometer and scanning the near infrared light ranges from, for instance 700 nm to 1000 nm and simultaneously recording changes in cytochrome c oxidase activity using a polarographic method. The wavelengths identified in FIG. 2A to directly or indirectly inhibit cytochrome c oxidase activity include 750 nm, 870 nm, 900 nm, and 950 nm. In addition, FIG. 2A illustrates a synergistic effect where dual wavelengths reduced respiration in both isolated cytochrome c oxidase and mitochondria. Of course, as previously discussed, other wavelengths, taken alone or in combination, of infrared light may inhibit cytochrome c oxidase besides those listed herein and shown in FIGS. 2A and 2B. Moreover, the wavelengths described herein are merely exemplary and may represent a range of frequencies centered around the frequency disclosed. For example, the wavelengths disclosed herein may be peak or middle wavelengths that represent a spectrum or range of wavelengths that reduce the effects of reperfusion injury. Indeed, additional wavelengths identified to inhibit cytochrome c oxidase may be found in one or more of the following exemplary wavelength ranges: 730-770 nm, 850-890 nm, 880-920 nm, or 930-970 nm. Furthermore, reducing reperfusion injury using light may be the result of a synergistic effect caused by the light source outputting a range or spectrum of wavelengths.

Not all wavelengths between 700 and 1000 nm inhibit cytochrome c oxidase. For example, as illustrated in FIG. 2B, a light source outputting light with a wavelength of approximately 810 nm may activate cytochrome c oxidase instead of inhibit cytochrome c oxidase. Activating cytochrome c oxidase would have the opposite effect than intended. Specifically, the inventors believe that activating cytochrome c oxidase could actually increase cell damage and cell death caused by, for instance, reperfusion injury. Therefore, a wavelength of 810 nm alone or in combination with one or more of the wavelengths in the ranges previously described that directly or indirectly inhibit cytochrome c oxidase may not produce the same benefits as using only wavelengths of light that inhibit cytochrome c oxidase. To the contrary, the wavelength of 810 nm may negate or reverse the effects of wavelengths that inhibit cytochrome c oxidase when applied prior to and/or during reperfusion. For at least this reason, the present treatment disclosed herein is distinguished from any prior treatment that applies light with a wavelength of or about 810 nm to ischemic tissue.

To analyze the effect of infrared light on cytochrome c oxidase, the enzyme may first be purified. Cytochrome c oxidase may be isolated from, for instance, cow tissues since large amounts (e.g., 300 g) may be required to obtain adequate yield of purified cytochrome c oxidase. Isolation of heart- and liver/brain-type cytochrome c oxidase using an optimized protocol may yield a regulatory-competent enzyme. The heart and liver/brain isozymes differ by the presence of three different isoform subunits: VIa, VIIa, and VIII. The catalytic subunits that contain the proposed infrared light photoacceptors, the heme and copper centers, are identical between the isozymes, which may explain why various wavelengths of infrared light are effective in both the heart and brain, as well as other tissues.

For each wavelength and combination of wavelengths, an energy-dose response curve can be established by varying the light output from 0-2 $W/cm^2$ and measuring cytochrome c oxidase activity using the polarographic method. After reaching a certain energy threshold, the inhibitory effect of infrared light may become saturated. Additional dose-response curves maybe recorded in the presence of the allosteric activator ADP and the allosteric inhibitor ATP including an ATP-regenerating system. Infrared light may affect cytochrome c oxidase in multiple ways. Thus, in addition to analyzing cytochrome c oxidase kinetics, proton pumping efficiency may also be assessed.

Following transient global cerebral ischemia, there is a morphological progression of neuronal injury that occurs in specific populations of neurons that are highly susceptible to damage and death. Hippocampal CA1 neurons are particularly sensitive to an ischemic insult, and a near-complete loss is observed at three to seven days after reperfusion in a rat animal model. Reactive oxygen species may play a role in the pathophysiology of neuronal death. Therefore, the neuroprotective effect of infrared light may be defined in terms of its ability to prevent degeneration of neurons in the CAI hippocampus. For instance, an experiment by the investigators using simulated brain ischemia in rats showed significant neuroprotection with infrared light treatment. Specifically, rats were exposed to eight minutes of global brain ischemia (bilateral carotid artery occlusion coupled with induced transient hypotension) with or without infrared light treatment for the final two minutes of ischemia and the first two hours of reperfusion using a device having a power output of approximately 200 $mW/cm^2$ and outputting light with wavelengths of approximately 750 nm, 870 nm, 900 nm, and 950 nm. This experiment revealed significant neuroprotection with infrared light treatment (e.g., rats treated with infrared light showed 66% protection, a greater than 10-fold increase in neuronal number versus the untreated group).

Figure 3:
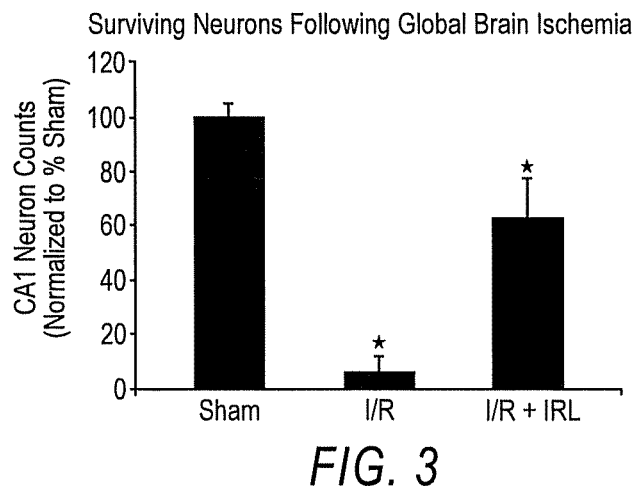
FIG. 3 is a graph illustrating exemplary neuron counts in the CA1 hippocampus of three groups of rats following an experiment testing treatments using low power diodes.
Figure 4:
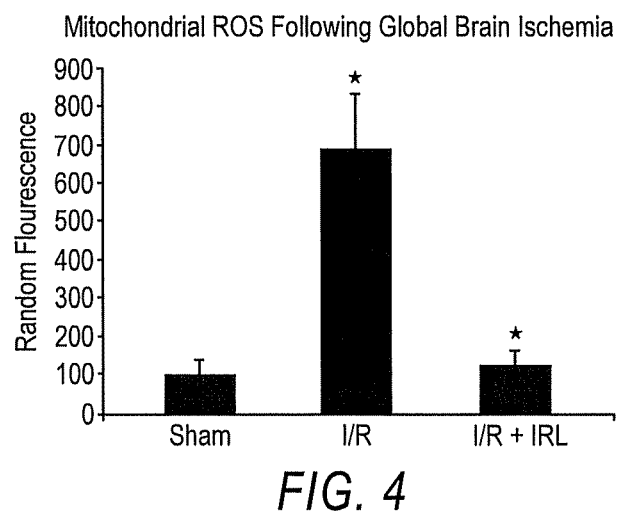
FIG. 4 is a graph of exemplary reactive oxygen species including superoxide production illustrating relative fluorescence following global brain ischemia of the three groups of rats following the experiment using lower power diodes.

FIGS. 3-7 are graphs that include various results following experiments of treatments perforned on rats. Specifically, FIG. 3 illustrates the neuron counts in the CA1 hippocampus of a non-ischemic sham-operated animal (Sham), a rat that underwent eight minutes of global brain ischemia followed by seven days of reperfusion (I/R), and a rat that underwent eight minutes of ischemia followed by seven days of reperfusion while being treated with infrared light (I/R+IRL) generated by low power diodes. FIG. 4 is a graph of superoxide production illustrating the relative fluorescence of the Sham, I/R, and I/R+IRL groups of rats following the experiment previously described. From these experiments, the rats that underwent the infrared light treatment had higher neuron counts (FIG. 3) and lower levels of mitochondrial reactive oxygen species (FIG. 4) than those rats that were simply subject to reperfusion following global brain ischemia.

Infrared light may further have a cardioprotective effect following myocardial ischemia/reperfusion. For instance, in an experiment performed by the inventors using rats, the rats underwent 45 minutes of left coronary artery occlusion followed by two hours of reperfusion. In the infrared light-treated rats, irradiation of the anterior wall of the heart (e.g., the area perfused by the left coronary artery) was initiated during the final ten minutes of occlusion and was maintained throughout the two-hour reperfusion period using a device having a power output of approximately 200 mW/cm$^2$ and outputting light with at least wavelengths of about 750 nm, 870 nm, 900 nm, and 950 nm. At the end of the experiment, infarct size was delineated by triphenyltetrazolium chloride staining and expressed as a percent of the risk region (e.g., the extent of the ischemic myocardial bed). This experiment revealed significant cardioprotection with infrared light treatment (e.g., infarct size in the treated versus control groups averaged 20+/−5% of the myocardium at risk versus 59+/−5% of the myocardium at risk, respectively).

Figure 5:
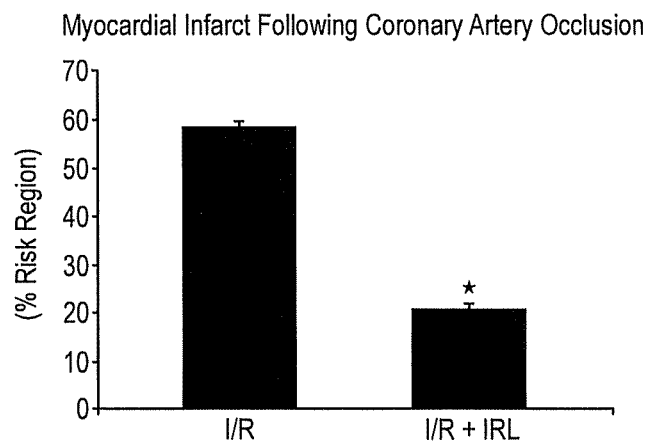
FIG. 5 illustrates myocardial infarct size of the I/R group of rats compared to a control group using low power diodes.
Figure 6:
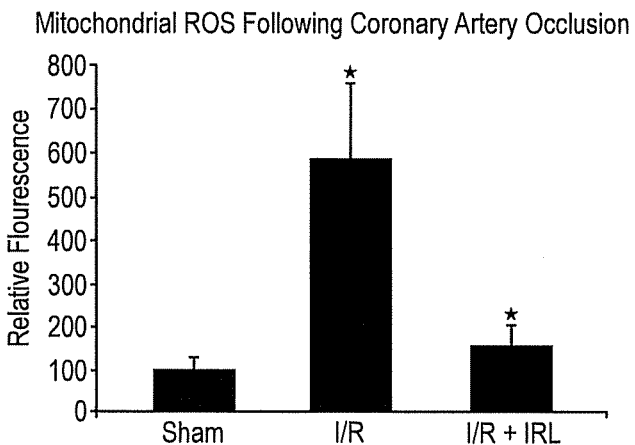
FIG. 6 is a graph illustrating relative fluorescence of exemplary reactive oxygen species including superoxide production following coronary artery occlusion of three groups of rats following the experiment using low power diodes.

FIG. 5 illustrates the myocardial infarct size of the rats in the I/R group versus the control group following coronary artery occlusion. FIG. 6 is a graph illustrating relative fluorescence of exemplary reactive oxygen species including superoxide production following coronary artery occlusion of the three groups of rats following the experiment. FIGS. 5 and 6 illustrate the benefits to rats that received the light treatment compared to rats that did not.

Figure 7:
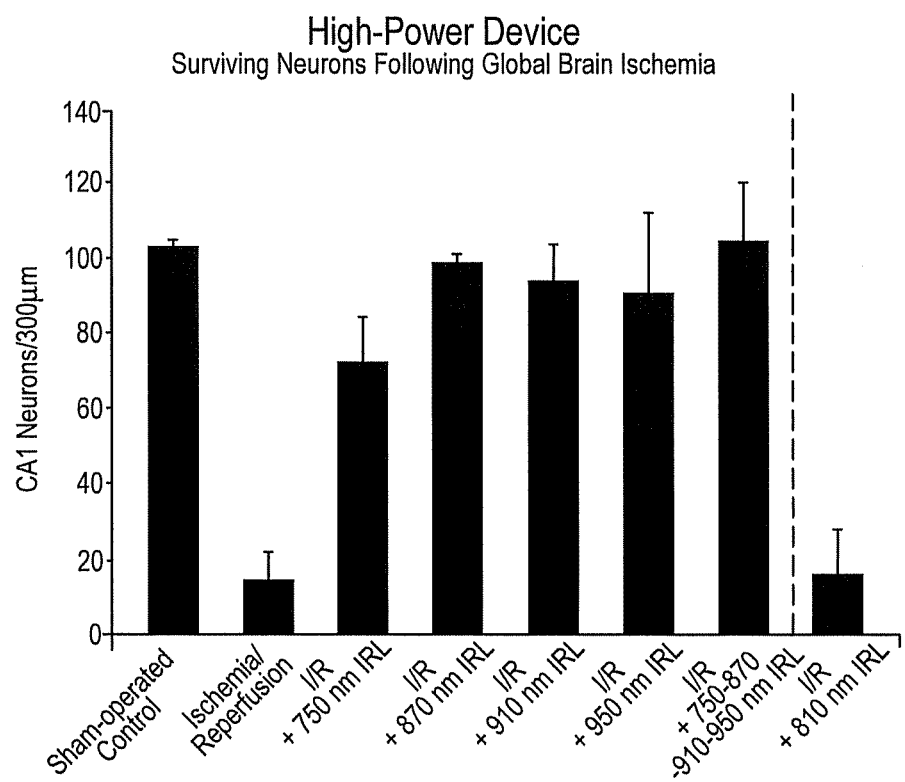
FIG. 7 is a graph illustrating exemplary neuron counts in the CA1 hippocampus of various groups of rats following treatments for global brain ischemia using high power diodes.

Tests using high power diodes generate similar results. For example, FIG. 7 is a graph illustrating exemplary neuron counts in the CA1 hippocampus of the various groups of rats following a light treatment for global brain ischemia using high power diodes. As illustrated, the rats that received the light treatment described herein had higher neuron counts following global brain ischemia than those that did not. Therefore, the inventors believe that both low power diodes and high power diodes provide beneficial effects when used with the treatment disclosed herein. Further, as illustrated, a wavelength of 810 nm does not result in improved neuron survival.

Figure 8:
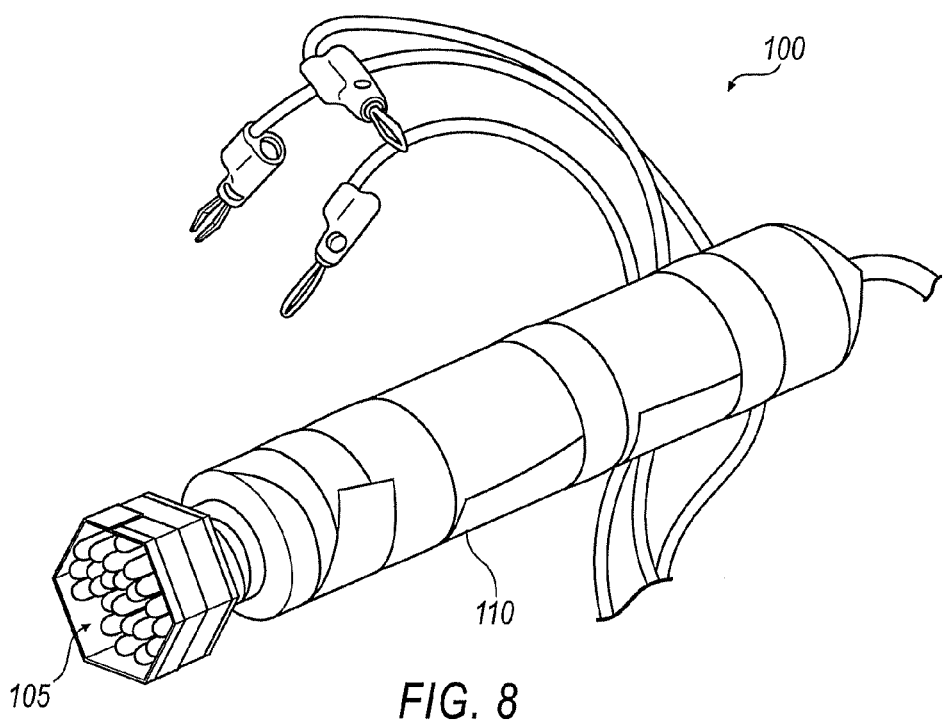
FIG. 8 illustrates an exemplary light therapy device that may be used to inhibit cytochrome c oxidase and reduce reperfusion injury.

FIG. 8 illustrates an exemplary light therapy device 100 that may be used to directly or indirectly inhibit cytochrome c oxidase using infrared light, and thus reduce reperfusion injury. The light therapy device 100 includes at least one light source 105 configured to output light at a wavelength that inhibits cytochrome c oxidase when the light is applied to an ischemic area of tissue before, during, and/or after reoxygenation or clinical intervention. The light source 105 may include a light emitting diode (LED), a laser diode, optical fibers, or any other source that is configured to emit light with a wavelength that, for instance, directly or indirectly inhibits cytochrome c oxidase when applied prior to reperfusion and at least partially during reperfusion. For instance, the light source 105 may include any light source 105 that is configured to output light with a wavelength of 750 nm, 870 nm, 900 nm, or 950 nm. Other light sources 105 may include quadruple diodes or a combination of individual wavelength diodes. Further, the light sources 105 may be high power or low power. The type of light source 105 may depend upon the application. For instance, optical fibers may be used to deliver light to areas of the body that may be difficult to reach with larger light sources and thus provide infrared treatment through the mouth, ears, nose, etc.

The light therapy device 100 may include any number of light sources 105, for instance, arranged in an array such as a diode array or a fiber optic array. Each of the light sources 105 in the array may output light with one of the wavelengths that inhibit cytochrome c oxidase. In one exemplary implementation, some of the light sources 105 in the array may output light with one wavelength while other light sources 105 in the array may output light with a different wavelength. Therefore, the light sources 105 in combination may output light having multiple wavelengths that inhibit cytochrome c oxidase and reduce reperfusion injury.

Moreover, the light sources 105 are configured to output light with a power density that is sufficient to at least partially penetrate one or more body tissues such as skin, bone, muscle tissue, and organs. In one exemplary approach, each light source 105 may be configured to output light with a power density of at least approximately 200 mW/cm$^2$. For instance, each light source 105 may be configured to output light with a power density of at least approximately 800 mW/cm$^2$ when used with an adult human. Alternatively, if the light therapy device 100 is used with, for example, a neonate, the power density may be lower than 200 mW/cm$^2$. One or more of the light sources 105 in the array may have a different power density than one or more of the other light sources 105 in the array. Further, the power density of each light source 105 may be related to the wavelength of light generated by the light source 105. Therefore, light sources 105 generating light with the same wavelength may be output with the same power density while light sources 105 generating light at different wavelengths may be output with different power densities.

The light therapy device 100 further includes a portion, such as a handle 110, that houses various electronics that allow the light sources 105 to operate correctly. For instance, the handle 110 may include one or more processors and circuit boards that control operation of the light sources 105, including enabling and disabling the light sources 105, adjusting the brightness of the light sources 105, etc. Alternatively, some of the electronics used to operate the light sources 105 may be housed in a separate device other than the light therapy device 100.

The light therapy device 100 illustrated is merely exemplary and may take other forms. For instance, the light therapy device may be incorporated into a helmet for brain treatments, a catheter for combined clot removal and infrared light treatment, a mouthpiece or toothbrush to treat dental/gum disorders, a massage device, diabetic socks or slippers, a headband to treat headaches, an eye mask to treat eye diseases, a glove to treat gout or arthritis, a laser pointer to treat locally (e.g., a cold sore), a cushion, a blanket, a belt, a foot bath, a belly belt to help, for example, women at risk for preterm birth, a back belt to treat back pain, or an infrared pill charged via induction to treat intestinal diseases, a tanning booth for cosmetic purposes (e.g., wrinkle reduction), etc. The light therapy device 100 may be further configured to perform other tasks than described. For instance, the light therapy device 100 may be configured to act as an oximeter and monitor oxygen. Alternatively, the light therapy device 100 may be configured to work with one or more oximeters. If so, the light therapy device 100 may include a controller that prevents light used during treatment from interfering with light used to measure oxygen saturation.

FIG. 9 illustrates an exemplary flowchart of a process 200 that may be used to reduce the risk of reperfusion injury following an ischemic event. Block 205 includes generating light using, for instance, one or more light sources 105. The light source 105 may include a light emitting diode (LED), an optical fiber, a laser, or any other light source 105 configured to output light having a wavelength that directly or indirectly inhibits cytochrome c oxidase. Furthermore, the light source 105 is configured to output light with a range that includes multiple wavelengths. One or more of the wavelengths in the range may inhibit cytochrome c oxidase to reduce reperfusion injury when applied before, during, and/or after reoxygenation of ischemic tissue. For instance, the light source 105 may output light with a wavelength of approximately 750 nm, 870 nm, 900 nm, or 950 nm. Additionally, the light source 105 may output light at one or more of these wavelengths, as well as other wavelengths that inhibit cytochrome c oxidase. Moreover, the light source 105 is configured to output light having a power density sufficient to penetrate one or more body tissues. For instance, the power density may be sufficient to penetrate one or more of bone, skin, muscle tissue, and organ tissue. In one exemplary approach, the light source 105 may generate the light with a power density of at least approximately 200 mW/cm$^2$. For example, the light source 105 may generate the light with a power density of at least approximately 800 mW/cm$^2$ when used on an adult human or less than 200 mW/cm$^2$ when used on, for instance, neonates.

Block 210 includes applying light to an ischemic area of tissue prior to reoxygenation of the tissue, such as before or during clinical intervention. As previously discussed, various wavelengths of infrared light, alone or in combination, inhibit cytochrome c oxidase when applied, for example, no later than the onset of reperfusion and at least partially during reperfusion, reducing the effects of reperfusion injury. In one exemplary approach, using the exemplary light therapy device 100 illustrated in FIG. 7, a physician may direct the light generated by the light source 105 toward the ischemic area of a patient's body prior to the onset of reperfusion or prior to initiating a clinical intervention. A clinical intervention may include, for example, administering a clot-busting drug, inflating/deflating an angioplasty balloon, resuscitation, transfusion, or administering vaso-active drugs, among others. As previously discussed, reperfusion is defined as the process where oxygen and other nutrients are restored to ischemic tissue. The onset of reperfusion is defined as the instant in which reperfusion begins. Prior to or no later than the onset of reperfusion, the physician may direct the light onto the patient's skin, and the light may pass through the patient's skin, bone, muscle tissue, organs, or any other tissue prior to reaching the ischemic area. The physician may apply glycerol to the patient's skin to help the light penetrate the patient's skin. Glycerol helps make the skin transparent to infrared light. Alternatively, before reperfusion, the physician may direct the light directly onto the ischemic area if the ischemic area is exposed (e.g., via a surgical opening).

Block 215 includes applying the light at least partially during reoxygenation. In addition to applying the light prior to reoxygenation as illustrated at block 210, applying the light to the tissue at least partially during reperfusion may further inhibit cytochrome c oxidase and further reduce the effects of, for instance, reperfusion injury. Much cellular damage occurs at the onset of reperfusion reasonably due to hyperactive OxPhos enzymes. Accordingly, applying the light at the onset of reperfusion and continuing to apply the light for some amount of time during reperfusion may further directly or indirectly inhibit cytochrome c oxidase and reduce cell death and damage. In some instances (e.g., brain ischemia), applying the light shortly after reperfusion begins may still reduce cell death and damage, but to a lesser degree than if the light were applied prior to the onset of reperfusion. In one exemplary implementation, the light may be applied until reperfusion is complete, or alternatively, the light may be applied for a predetermined amount of time relative to when reoxygenation began. For instance, the physician may continue to apply the light for two hours following the onset of reperfusion.

Block 220 includes inhibiting cytochrome c oxidase using the light from the light therapy device 100. As previously discussed, applying light at various frequencies to ischemic tissue prior to and at least partially during reoxygenation or clinical intervention directly or indirectly inhibits cytochrome c oxidase. The inventors believe that inhibiting cytochrome c oxidase indirectly prevents the generation of free radicals that may trigger cellular death and damage the affected tissues. As previously discussed, cytochrome c and the cytochrome c oxidase enzyme include photoacceptors that receive the light generated by the light therapy device 100. When the light output by the light therapy device 100 penetrates the various body tissues and reaches the ischemic area, the light inhibits cytochrome c oxidase and thus reduces cell damage caused by ischemia and reperfusion injury.

Block 225 includes gradually reducing the light to the treated tissue. For instance, the light output by the light therapy device 100 may be gradually reduced following the onset of reperfusion or after reperfusion is complete. In one exemplary approach, the physician may manually reduce the light output of the light therapy device 100 by disabling one or more of the light sources 105 in the array or by moving the light therapy device 100 further away from the patient. Alternatively, the light therapy device 100 may be configured to gradually reduce the brightness of one or more of the light sources 105 or disable the light sources 105 one at a time or in discrete groups so that the light applied to the ischemic area is automatically reduced.

FIG. 10 illustrates an exemplary flowchart of a process 300 that may be used to design a device configured to inhibit cytochrome c oxidase, such as the light therapy device 100 illustrated in FIG. 8.

Block 305 includes selecting at least one light source 105. The light source 105 is configured to generate light having a wavelength that, for example, inhibits cytochrome c oxidase during reoxygenation of ischemic tissue. The selected light source 105 may generate light having a wavelength that includes one or more of approximately 750 nm, 870 nm, 900 nm, and 950 nm. Selecting the light source 105 may further include arranging a plurality of light sources 105 in an array. In this exemplary approach, each of the light sources 105 may have a wavelength that inhibits cytochrome c oxidase during reoxygenation of ischemic tissue. Some light sources 105 in the array may be selected to include different wavelengths than other light sources 105 in the array. For instance, some of the light sources 105 may output light with a wavelength of about 750 nm, some of the light sources 105 may output light with a wavelength of about 870 nm, some of the light sources 105 may output light with a wavelength of about 900 nm, and some of the light sources 105 may output light with a wavelength of about 950 nm. Of course, other wavelengths of light may inhibit cytochrome c oxidase and may be used in the array. Also, the array need not include equal numbers of each type of light source 105.

Block 310 includes selecting a power density of the light source 105 sufficient for the light generated by the light source 105 to penetrate a body tissue. If the light sources 105 are arranged in an array, one or more of the light sources 105 may output light with a different power density than another of the light sources 105. The power density may further depend upon how the light is applied by the physician. For instance, if the physician applies the light to the patient through the patient's skin, bone, muscle tissue, and organs, then a higher power density may be necessary than if the light is applied directly to the ischemic tissue through, for instance, a surgical opening. Another consideration when selecting power density may include reducing the amount of thermal damage to the patient. For instance, the power density may be selected so that the tissue to which the treatment is applied does not heat by more than one degree Celsius during the treatment. In one exemplary approach, the power density may, for instance, be at least approximately 200 mW/cm$^2$. In another exemplary approach, for instance in an adult human patient, the power density may be at least approximately 800 mW/cm². However, the power density may be lower than 200 mW/cm² when used with other human patients, such as neonates.

The treatment previously described may have various applications. For instance, the treatment may be used to treat any tissue damage resulting from increased reactive oxygen species and/or conditions where reduction of cellular energy is favorable. As previously discussed, the apparatus and methods described herein may reduce the effects of ischemia and reperfusion injury (e.g., heart attack and stroke). In addition, the apparatus and methods may be beneficial during organ transplantation, during any surgery that involves transient interruption from blood supply such as a bypass surgery and other heart surgeries, when treating trauma including brain and spinal cord trauma, during wound healing such as in patients with diabetes, when treating neonatal brain hypoxia/ischemia or acute tubular necrosis, during cosmetic procedures (e.g., wrinkle reduction), during preterm birth and prenatal care (e.g., necrotizing enterocolitis), when treating pain such as back pain, etc. The apparatus and methods described herein may further be used to treat muscle spasms, asthma, epilepsy, erectile dysfunction, insomnia, abdominal and cerebral aneurysms, or inflammation and other diseases with increased reactive oxygen species including eye diseases such as uveitis, diabetic retinopathy, or cataracts, gum inflammation, arthritis, atherosclerosis, burns, viral infections such as cold sores or herpes, balding or gray hair, allergies, autoimmune disorders (e.g., systemic lupus), dermatitis, Crohn's disease, dicubity (e.g., bedsores), etc. The present disclosure may further reduce neurodegeneration such as that caused by Alzheimer's disease, Parkinson's disease, multiple sclerosis, or amyotrophic lateral sclerosis (ALS). The treatment described herein may have additional uses besides those explicitly disclosed, including additional uses in human and/or veterinary medicine.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the invention is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A light therapy device comprising:
a first light source configured to generate light with a first wavelength including 730-770 nm;
a second light source configured to generate light with a second wavelength including 950-970 nm; and
a processor configured to operate the first and second light sources to inhibit cytochrome c oxidase when applied to organic tissue in response to an ischemia-reperfusion event,
wherein the first and second wavelengths are applied at a power density that penetrates tissue of a human patient;
wherein the processor is configured to:
reduce a brightness of the light generated to inhibit cytochrome c oxidase following the inset of reperfusion;
reduce the drightness by individually disabling the light sources at different times; and reduce the brightness by disabling discrete groups of the light sources at different times.

2. A light therapy device as set forth in claim 1, wherein the light therapy device includes:
a third light source configured to generate light with at least a third wavelength including 850-890 nm; and
a fourth light source configured to generate light with at least a fourth wavelength including 880-920 nm.

3. A light therapy device as set forth in claim 1, wherein the processor is configured to operate the first and second light sources during ischemia, at the onset of reperfusion, after reperfusion, or any combination thereof.

4. A light therapy device as set forth in claim 3, wherein the processor is configured to operate the first and second light sources for at least two consecutive hours following the onset of reperfusion.

5. A light therapy device as set forth in claim 1, wherein the processor is configured to output power densities that are different for each light source.

6. A light therapy device as set forth in claim 1, wherein each light source includes a power density ranging from approximately 200 mW/cm² to approximately 800 mW/cm².

7. A light therapy device as set forth in claim 1, wherein the light therapy device is configured to work with one or more oximeters to monitor oxygen, and the light therapy device further comprises a controller that is configured to prevent light generated during treatment from interfering with light used to measure oxygen saturation.

8. A light therapy device comprising:
light sources configured to generate light in four different wavelengths, each wavelength being selected respectively from ranges 730-770 nm, 850-890 nm, 880-920 nm, and 950-970 nm; and
a processor configured to control operation of at least two of the different wavelengths of the light therapy device to inhibit cytochrome c oxidase when applied to organic tissue during ischemia, at the onset of reperfusion, after reperfusion, or any combination thereof, and apply each of the different wavelengths at a power density that penetrates tissue of a human patient; wherein the processor is configured to reduce a brightness of the light generated to inhibit cytochrome c oxidase; and wherein the processor reduces the brightness by individually disabling the light sources at different times.

9. A light therapy device as set forth in claim 8, wherein the light includes a wavelength of approximately 750 nm, approximately 870 nm, approximately 900 nm, and approximately 950 nm.

10. A light therapy device as set forth in claim 8, wherein the light is generated by at least one of a light emitting diode, an optical fiber, and a laser.

11. A light therapy device as set forth in claim 8, wherein the light therapy device includes light sources that are each configured to generate the different wavelengths of light that inhibit cytochrome c oxidase, and wherein the processor controls the light sources such that a power density is different for each light source.

12. A light therapy device as set forth in claim 8, wherein each light source includes a power density ranging from approximately 200 mW/cm$^2$ to approximately 800 mW/cm$^2$.

13. A light therapy device as set forth in claim 8, wherein the light therapy device is configured to work with one or more oximeters to monitor oxygen, and the light therapy device further comprises a controller that is configured to prevent light generated during treatment from interfering with light used to measure oxygen saturation.

14. A light therapy system comprising: light sources configured to generated light at wavelengths including 730-779 nm, and 950-970 nm, that inhibits cytochrome c oxidase and at a power density that penetrates the tissue of a patient adjacent to an ischemia-reperfusion event, wherein the light therapy system is configured to monitor oxygen; and a controller configured to prevent light generated during treatment from interfering with light used to measure oxygen saturation; further comprising a processor configured to: reduce a brightness of the light emitted following the onset of reperfusion; and reduce the brightness by individually disabling the light sources at different times.

15. A light therapy system as set forth in claim 14, further comprising the light sources configured to emit light at different wavelengths, wherein the light sources apply light at power densities that penetrates the bone of a human patient.

16. A light therapy system as set forth in claim 15, wherein each of the light sources includes a power density ranging from approximately 200 mW/cm$^2$ to approximately 800 mW/cm$^2$.

17. A light therapy system as set forth in claim 15, wherein the processor is further configured to output a power density that is different for each of the light sources.

18. A light therapy system as set forth in claim 14, wherein the light sources include additional light sources that generate light at a wavelength including 850-890 nm, and at a wavelength including 880-920 nm.

* * * * *

UNITED STATES PATENT AND TRADEMARK OFFICE
CERTIFICATE OF CORRECTION

PATENT NO. : 8,945,196 B2
APPLICATION NO. : 12/771137
DATED : February 3, 2015
INVENTOR(S) : Maik Huttemann et al.

It is certified that error appears in the above-identified patent and that said Letters Patent is hereby corrected as shown below:

In the Claims

At column 12, claim number 1, line number 21, the word "drightness" is incorrect and should be deleted. The correct word is "brightness".
The claim should read, "reduce the brightness by individually disabling the light ..."

At column 13, claim number 14, line number 24, "730-779 nm" is incorrect and should be deleted. The correct phrase is "730-770 nm".
The claim should read, "... at wavelengths including 730-770 nm, and 950-970 nm ..."

Signed and Sealed this
Second Day of June, 2015

Michelle K. Lee
*Director of the United States Patent and Trademark Office*